(12) United States Patent
Lee

(10) Patent No.: US 9,039,642 B2
(45) Date of Patent: May 26, 2015

(54) NOZZLE SEPARATING STRUCTURE OF ORAL IRRIGATOR

(76) Inventor: Young Hoon Lee, Seoul (KR)

( * ) Notice: Subject to any disclaimer, the term of this patent is extended or adjusted under 35 U.S.C. 154(b) by 783 days.

(21) Appl. No.: 13/286,793

(22) Filed: Nov. 1, 2011

(65) Prior Publication Data

US 2013/0089832 A1 Apr. 11, 2013

(30) Foreign Application Priority Data

Oct. 6, 2011 (KR) .................. 10-2011-0101543

(51) Int. Cl.
*A61C 17/00* (2006.01)
*A61C 17/02* (2006.01)

(52) U.S. Cl.
CPC .................. *A61C 17/0202* (2013.01)

(58) Field of Classification Search
CPC ........................................ A61C 17/02
USPC .............. 601/154, 160, 162, 163, 165, 169; 433/80, 81, 82, 89; 604/19, 30, 32, 43
See application file for complete search history.

(56) References Cited

U.S. PATENT DOCUMENTS

| | | | |
|---|---|---|---|
| 5,626,472 A * | 5/1997 | Pennetta | 433/80 |
| 6,156,017 A * | 12/2000 | Shieh | 604/19 |
| 6,689,078 B1 * | 2/2004 | Rehkemper et al. | 601/162 |
| 6,783,505 B1 * | 8/2004 | Lai | 601/162 |
| 2007/0073199 A1 * | 3/2007 | Shaw | 601/165 |

FOREIGN PATENT DOCUMENTS

| | | |
|---|---|---|
| KR | 1020060089558 A | 8/2006 |
| KR | 20-0432170 | 11/2006 |
| KR | 100905158 B1 | 6/2009 |

* cited by examiner

*Primary Examiner* — Quang D Thanh
(74) *Attorney, Agent, or Firm* — Lucas & Mercanti, LLP

(57) ABSTRACT

A structure for separating a discharge nozzle of an oral irrigator includes a first discharge path formed in one side of the irrigator body, a water pressure control lever rotatably arranged above the first discharge path and having a second discharge path in the other side of the irrigator body, a release button section provided on an upper portion of the water pressure control lever and into which the discharge nozzle is inserted and engaged, and configured, when pushed, to be bent so as to release the engaged discharge nozzle, and a locking section provided in the release button section and water pressure control lever to control a pushing operation of the release button section depending upon whether the first discharge path is open or blocked.

7 Claims, 9 Drawing Sheets

NOZZLE SEPARATING STRUCTURE OF ORAL IRRIGATOR

CROSS-REFERENCE TO RELATED APPLICATION

This patent application claims the benefit of priority under 35 U.S.C. §119 from Korean Patent Application No. 10-2011-0101543, filed on Oct. 6, 2011, the contents of which are incorporated herein by reference.

BACKGROUND OF THE INVENTION

1. Field of the Invention

The present invention relates, in general, to a structure for separating a discharge nozzle of an oral irrigator and, more particularly, to a structure for separating a discharge nozzle of an oral irrigator, which prevents the discharge nozzle from separating when a discharge path is being open, and allows the same to be disassembled when the discharge path is blocked.

2. Description of the Related Art

Generally, an oral irrigator is used to spray the teeth and the gums with a stream of pressurized water so as to remove food debris between the teeth, remove tartar or harmful bacteria between the teeth and the gum, remove foreign substances stuck to orthodontic appliances, or massage the gum.

A type of oral irrigator is one in which an irrigator body and a discharge nozzle are integrated into a piece, although they are separable from each other. The structure of the separable type oral irrigator is configured such that the discharge nozzle is detachably coupled to the irrigator body, and is separated from the irrigator body in response to the pushing of a release button.

However, if the release button is pushed by mistake while cleaning water is being sprayed through the discharge nozzle, the discharge nozzle is separated from and shot out of the irrigator body by the water pressure of the cleaning water. This may cause the problems of injuring the mouth or face of the user whose mouth is being cleaned with the irrigator, the cleaning water which is sprayed in all directions getting the user wet, or the discharge nozzle which is shot off being broken when it falls onto the floor.

SUMMARY OF THE INVENTION

Accordingly, the present invention has been made keeping in mind the above problems occurring in the related art, and an object of the present invention is to provide a structure for separating a discharge nozzle of an oral irrigator, which when a discharge path is being open, prevents a release button from being pushed so that the discharge nozzle cannot be disassembled, and when the discharge path is blocked, allows the release button to be pushed so that the discharge nozzle can be disassembled, thereby ensuring safety when the oral irrigator is being used.

In order to achieve the above objects, according to one aspect of the present invention, there is provided a structure for separating a discharge nozzle of an oral irrigator from an irrigator body, the structure including: a first discharge path formed in one side of the irrigator body from the central line of the irrigator body; a water pressure control lever rotatably arranged above the first discharge path and having a second discharge path in the other side of the irrigator body from the central line, thereby opening and blocking the first discharge path; a release button section provided on an upper portion of the water pressure control lever and into which the discharge nozzle is inserted and engaged at a central portion thereof, and configured, when an outer surface thereof is pushed, to be bent so as to release the engaged discharge nozzle; and a locking section provided in the release button section and water pressure control lever to control a pushing operation of the release button section depending upon whether the first discharge path is opened or blocked.

Here, the release button section includes a leaf spring part which is provided at the central portion and with which the discharge nozzle is engaged, a button part connected to one side of the leaf spring part and designed, when pushed, to bend the leaf spring part so as to enlarge an inner diameter of the leaf spring part, and a cover part covering the leaf spring part such that the button part protrudes to the outside and having an upper opening through which the discharge nozzle is inserted.

The locking section includes a locking groove of a certain length that extends along a circumference of the water pressure control lever, a locking release groove integrally connected to one end of the locking groove, and a locking bar vertically protruding from an undersurface of the release button section such that the locking bar is inserted into and positioned at the locking groove or locking release groove as the water pressure control lever rotates, so as to control the pushing operation of the release button section.

The water pressure control lever has an irregular outer surface in order to facilitate rotation and control of the water pressure control lever.

According to another aspect of the present invention, there is provided a structure for separating a discharge nozzle of an oral irrigator from an irrigator body, the structure including: a first discharge path formed in one side of the irrigator body from the central line of the irrigator body; a water pressure control lever including an outer lever part having a second discharge path formed in line with the first discharge path and a central hollow receiving section, one side of which is open, being formed into a dual layer structure of upper and lower layers, and a central lever part rotatably coupled into the receiving section and having a third discharge path in the other side of the irrigator body from the central line, thereby opening and blocking the first and second discharge paths; a release button section provided on an upper portion of the water pressure control lever and into which the discharge nozzle is inserted and engaged at a central portion thereof, and configured, when an outer surface thereof is pushed, to be bent so as to release the engaged discharge nozzle; and a locking section provided in the release button section and water pressure control lever to control a pushing operation of the release button section depending upon whether the first and second discharge paths are opened or blocked.

Here, the locking section includes a locking groove of a certain length that extends along circumferences of the outer lever part and central lever part, a locking release groove integrally connected to one end of the locking groove and having a width larger than that of the locking groove, and a locking bar vertically protruding from an undersurface of the release button section such that the locking bar is inserted into and positioned at the locking groove or locking release groove as the central lever part rotates, so as to control the pushing operation of the release button section.

The release button section includes a leaf spring part which is provided at the central portion and with which the discharge nozzle is engaged, a button part connected to one side of the leaf spring part and designed, when pushed, to bend the leaf spring part so as to enlarge an inner diameter of the leaf spring part, and a cover part covering the leaf spring part such that the button part protrudes to the outside and having an upper opening through which the discharge nozzle is inserted.

According to the structure for separating the discharge nozzle for an oral irrigator, when cleaning water is sprayed through the discharge nozzle, the release button section cannot be pushed so that the discharge nozzle cannot be disassembled, and when the cleaning water is not being sprayed through the discharge nozzle, the release button section can be pushed so that the discharge nozzle can be disassembled, thereby solving the problem of the discharge nozzle being separated from and shot out of the irrigator body and therefore improving its safety when used.

Further, water pressure that is being sprayed can be easily regulated, and the discharge nozzle can be easily mounted and dismounted, thereby providing the effect of improving the convenience of use.

BRIEF DESCRIPTION OF THE DRAWINGS

The above and other objects, features and further advantages of the present invention will be more clearly understood from the following detailed description when taken in conjunction with the accompanying drawings, in which:

FIGS. 5A to 5C are cross-sectional plan views showing the structure in the state of the discharge paths changing from a disconnected state to a connected state and of the locking section changing from an unlocked state to a locked state, wherein

DETAILED DESCRIPTION OF THE INVENTION

Figure 1:
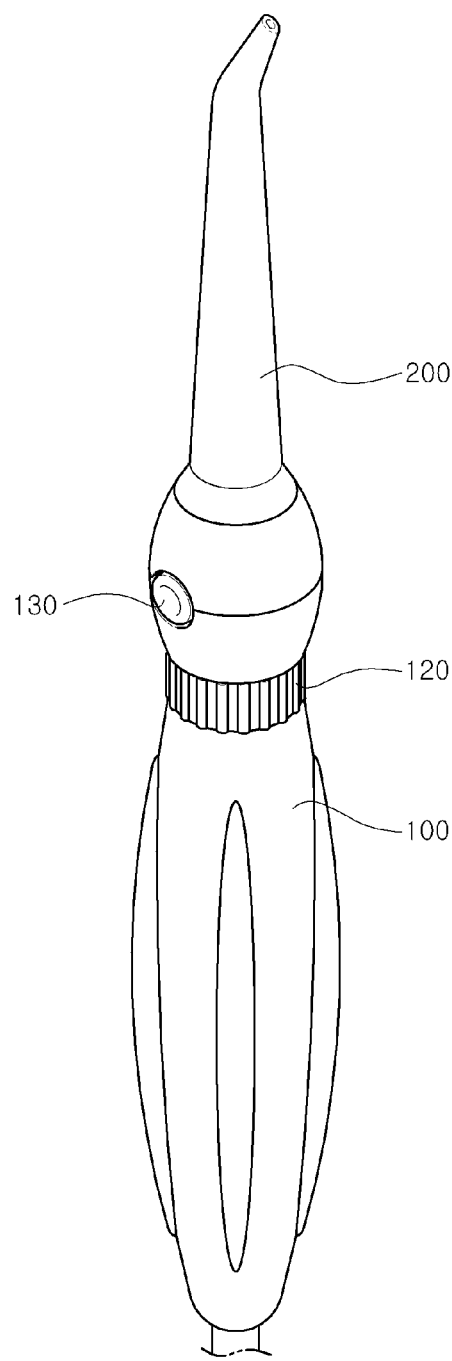
FIG. 1 is a perspective view showing a structure for separating a discharge nozzle of an oral irrigator according to an embodiment of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
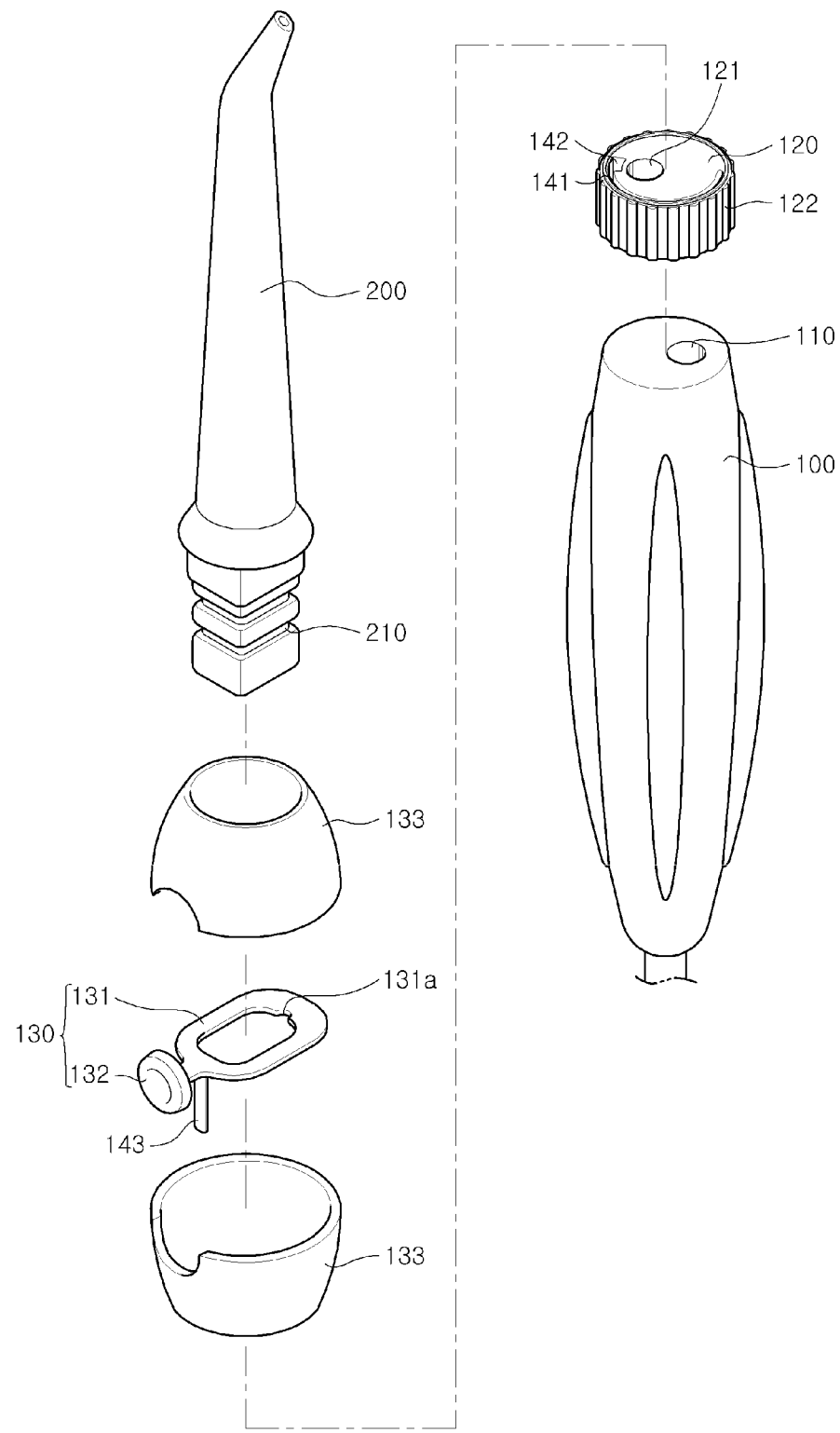
FIG. 2 is an exploded perspective view showing the structure for separating the discharge nozzle.
Figure 3:
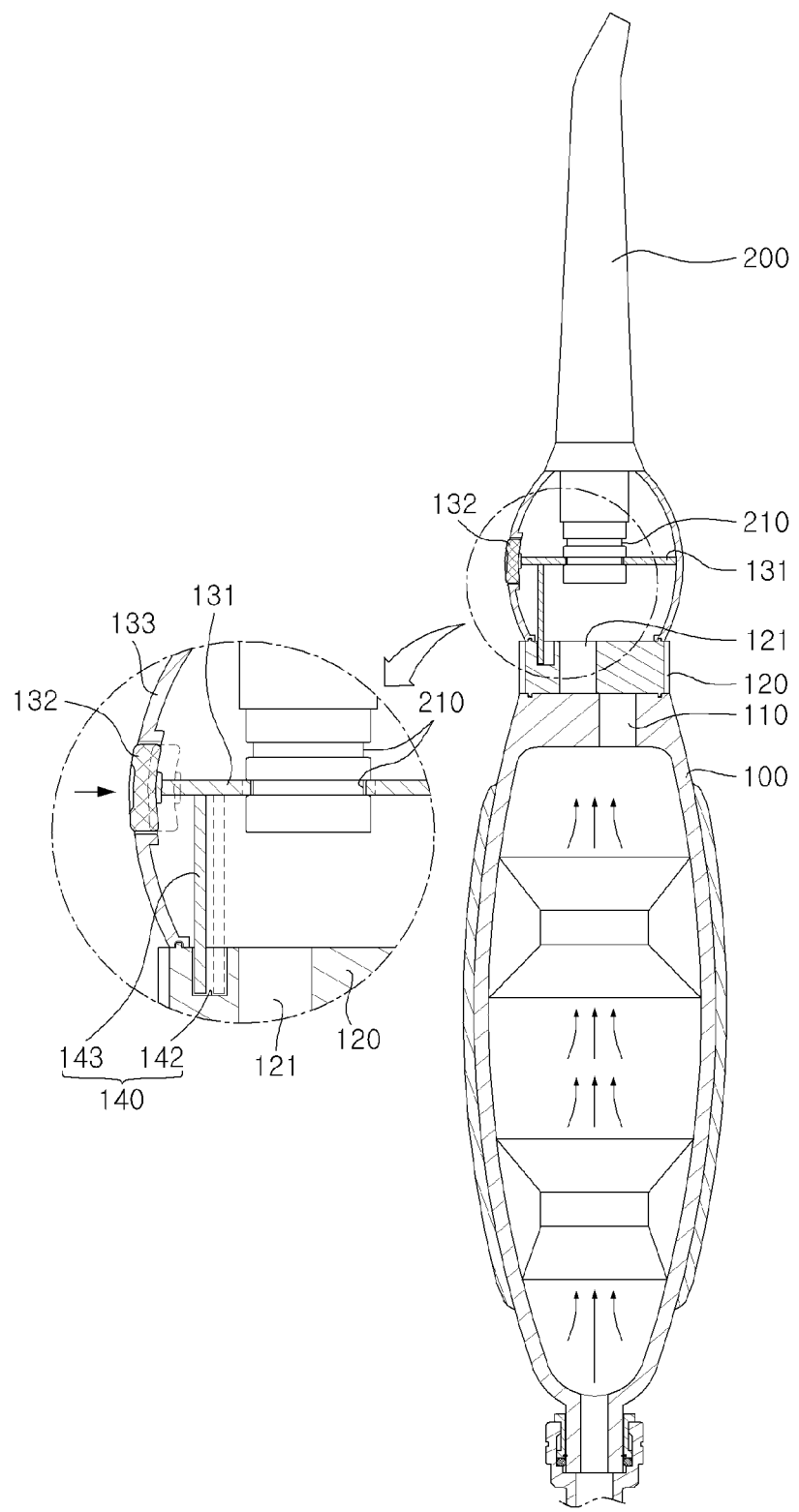
FIG. 3 is a cross-sectional view showing the structure in the state of the discharge paths being blocked.
Figure 4:
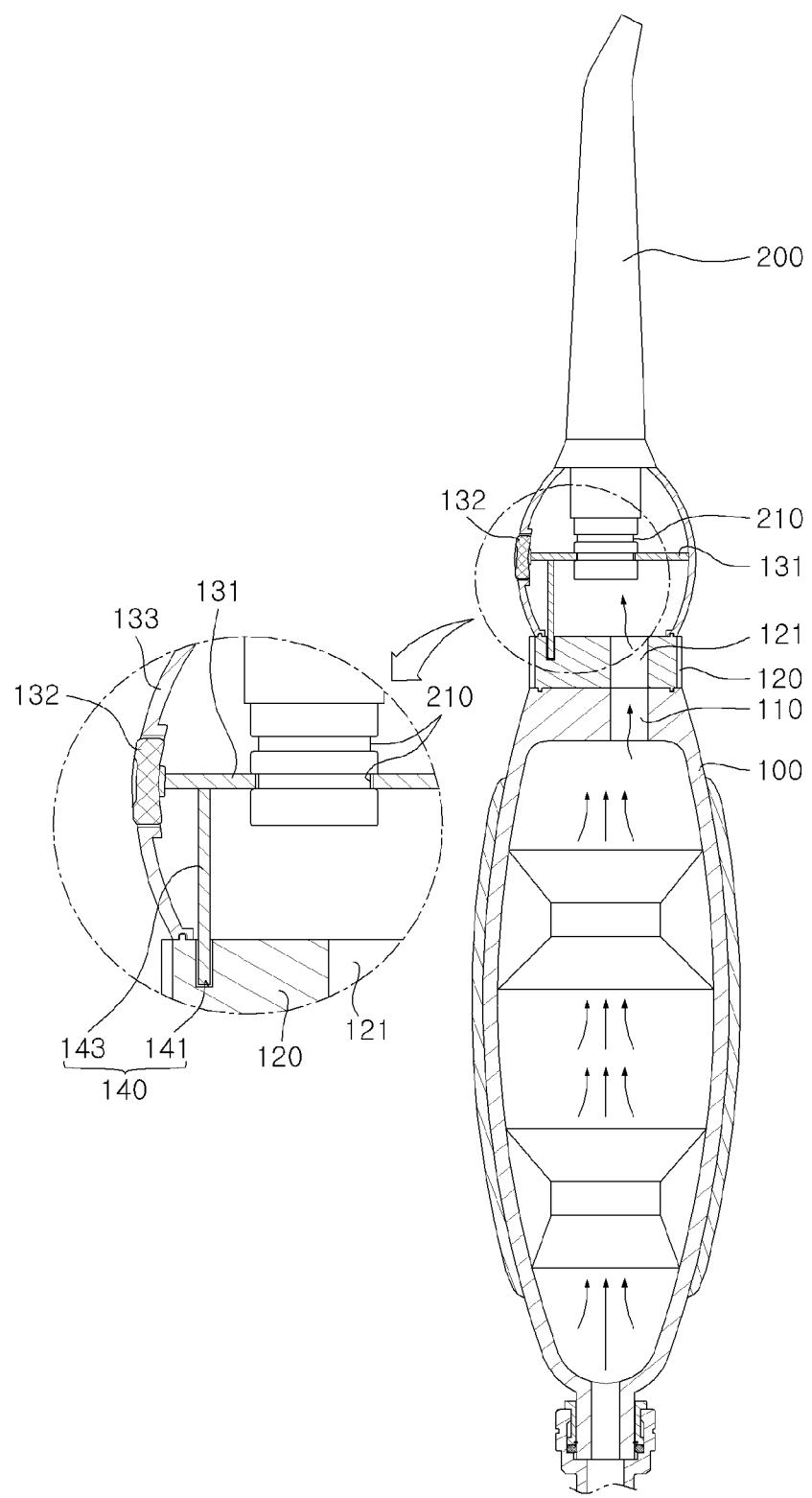
FIG. 4 is a cross-sectional view showing the structure in the state of the discharge paths being open.
Figure 5A:
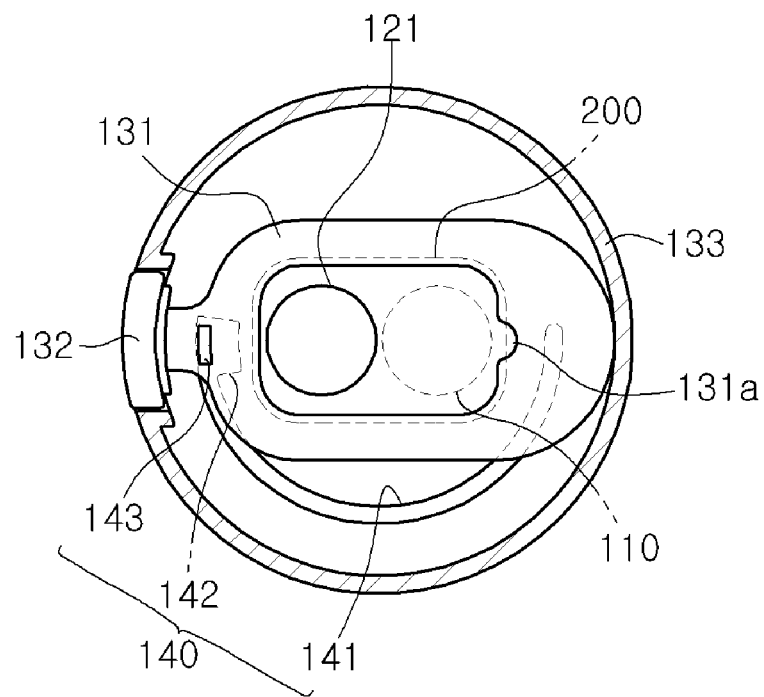
Figure 5B:
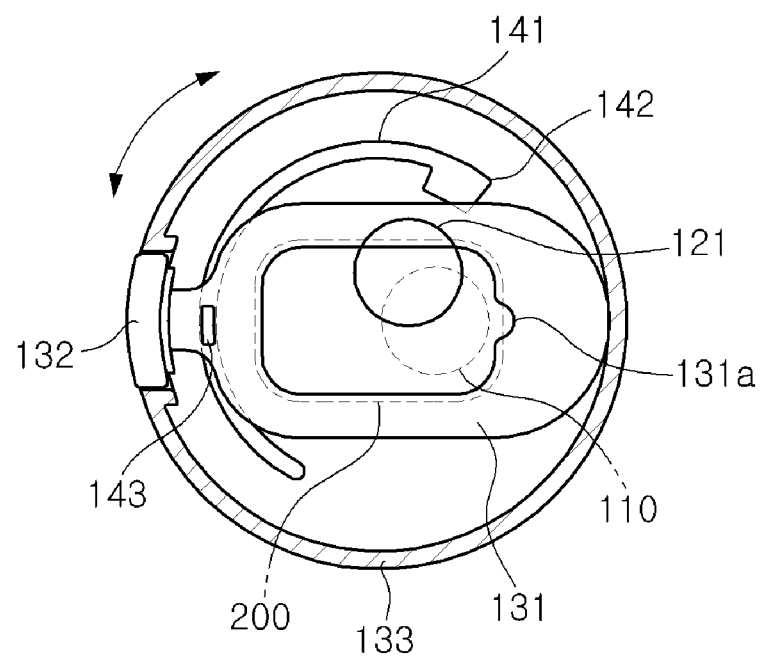
Figure 5C:
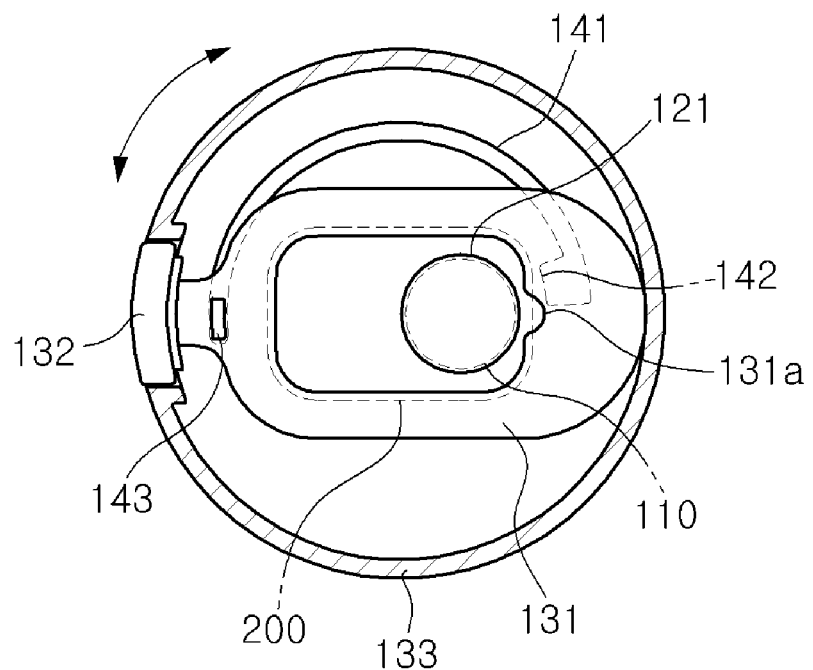
Figure 5D:
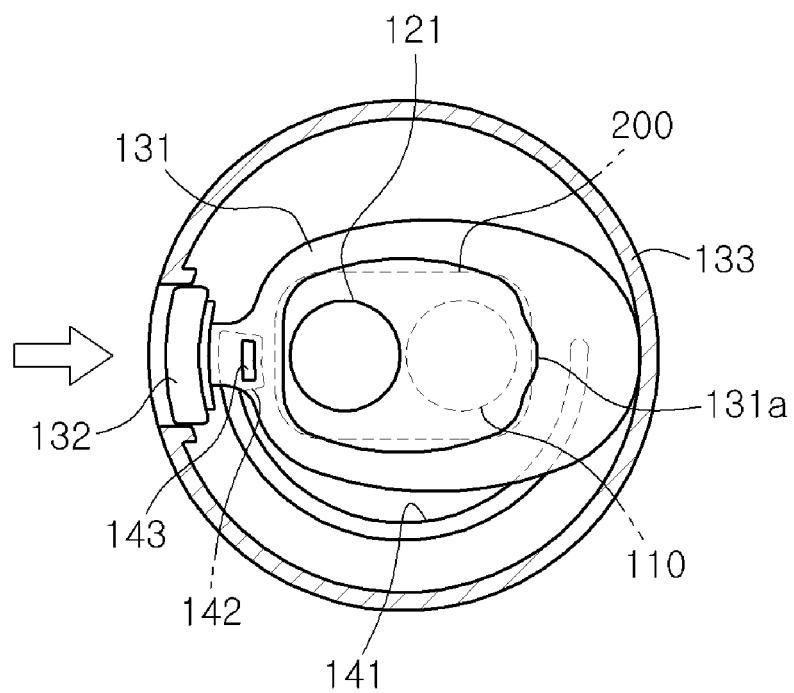
FIG. 5D shows the state of a button section being pushed when in the state of FIG. 5A.

FIG. 1 is a perspective view showing a structure for separating a discharge nozzle of an oral irrigator according to an embodiment of the present invention, FIG. 2 is an exploded perspective view showing the structure for separating the discharge nozzle, FIG. 3 is a cross-sectional view showing the structure in the state of the discharge paths being blocked, FIG. 4 is a cross-sectional view showing the structure in the state of the discharge paths being open, and FIGS. 5A to 5C are cross-sectional plan views showing the structure in the state of the discharge paths changing from a disconnected state to a connected state and of the locking section changing from an unlocked state to a locked state, wherein FIG. 5D shows the state of a button section being pushed when in the state of FIG. 5A.

As shown in FIGS. 1 to 4, the structure for separating a discharge nozzle of an oral irrigator includes a first discharge path 110 formed in an irrigator body 100, a water pressure control lever 120, a release button section 130, and a locking section 140.

The first discharge path 110 formed in the irrigator body 100 is provided in one side of the irrigator body 100 from the central line of the irrigator body 100.

The water pressure control lever 120 is provided on an upper portion of the first discharge path 110 of the irrigator body 100 and below the release button section 130 to be described later, such that it is rotatably coupled between the release button section 130 and the first discharge path 110 of the irrigator body 100. The water pressure control lever 120 is provided with a second discharge path in the other side from the central line of the irrigator body adjacent to the first discharge path 110. In addition, the water pressure control lever 120 has an irregular outer surface 122 in order to facilitate rotation and control of the water pressure control lever.

The release button section 130 includes a leaf spring part 131 which is provided at the central portion of the release button section above the water pressure control lever 120 and with which a discharge nozzle 200 is inserted into and engaged, a button part 132 which is connected to one side of the leaf spring part 131 and designed, when pushed, to bend the leaf spring part 131 so as to enlarge an inner diameter of the leaf spring part 131, and a cover part 133 which covers the leaf spring part 131 such that the button part 200 protrudes to the outside and which has an upper opening through which the discharge nozzle 200 is inserted.

Here, the discharge nozzle 200 has a coupling groove 210 in an outer circumferential surface of one end thereof, and is interference-fitted into the central portion of the lead spring part 131. Thus, an inner portion of the leaf spring part 131 is fitted into the coupling groove 210 of the discharge nozzle 200, thereby fixing the discharge nozzle 200.

Then, the leaf spring part 131 becomes bent when the opposite portion of the button section 132 comes into contact with an inner wall of the cover part 133 and the button section is pushed. Here, the leaf spring part 131 may preferably be provided with an enlarging groove 131a, which is recessed from an inner side of the leaf spring part in order to allow an inner diameter of the leaf spring part to enlarge when it is bent. In addition, the leaf spring part may consist of a plurality of leaf spring parts depending upon the number of coupling grooves of the discharge nozzle.

Further, the button section 132 protrudes to the outside of the cover part 133 such that it can be pushed by the finger of a hand holding the irrigator body 100.

The locking section 140 includes a locking groove 141 of a certain length which extends along a circumference of the water pressure control lever 120, a locking release groove 142 which is integrally connected to one end of the locking groove 141, and a locking bar 143 which vertically protrudes from an undersurface of the release button 130 such that the locking bar is inserted into and positioned at the locking groove 141 or locking release groove 142 as the water pressure control lever 120 rotates, so as to control the pushing operation of the release button section 130.

Here, the length of the locking groove 141 amounts to that of a radius of water pressure control lever 120 such that adjacent first and second discharge paths 110 and 121 provided in opposite sides of the central line overlap and become connected to each other. Further, the width of the locking groove is formed such that the locking bar 143 is inserted into and merely moved not in the width direction, but along the longitudinal direction of the locking groove. Further, the locking release groove 142 provided in one side of the locking groove 141 has a width larger than that of the locking groove 141 such that the locking bar 143 inserted into the locking release groove can move in the width direction of the locking release groove.

The operation of the structure for separating the discharge nozzle of an oral irrigator will now be described.

First, as shown in FIGS. 3 and 5A, in the state of the first discharge path 110 of the irrigator body 100 being blocked, when the water pressure control lever 120 rotates in one direction, as shown in FIGS. 4 and 5B, the second discharge path 121 formed in the water pressure control lever 120 rotates about the central line of the water pressure control lever 120 and gradually overlaps with the upper portion of the first discharge path 110, thereby sequentially opening the first discharge path. Concurrently with the opening of the first discharge path 110, the locking bar 143 of the locking section 140 is positioned in the locking groove 141 so that the button section 132 cannot be pushed. With this interruption on the pushing operation of the button section 132, the leaf spring part 131 is maintained in the state of being engaged with the coupling groove 210 of the discharge nozzle 200, thereby preventing the discharge nozzle 200 from being disassembled. Further, as shown in FIG. 5C, when the second discharge path 121 overlaps and is connected with the upper portion of the first discharge path 110, the water pressure of cleaning water reaches a maximum, and if one wants to reduce the water pressure, the water pressure control lever 120 is rotated in the opposite direction so as to gradually block the first discharge path 110, thereby reducing the water pressure of the cleaning water.

In addition, as shown in FIG. 5D, when the water pressure control lever 120 is rotated to the end in the opposite direction so as to completely block the first discharge path 110, the locking bar 143 of the locking section 140 is positioned in the locking release groove 142, thereby being in the state of the button section 132 being possibly pushed. That is, when one wants to disassemble the discharge nozzle 200, if the button section 132 is pushed, the outside of the leaf spring part 131 is put under pressure which causes the leaf spring part 131 to bend, which causes the inner diameter of the leaf spring part 131 to increase, being in the state of the leaf spring part being partially disengaged from the coupling groove 210 of the discharge nozzle 200. In this state, if the discharge nozzle 200 is drawn out, the discharge nozzle 200 can be easily disassembled.

Figure 6:
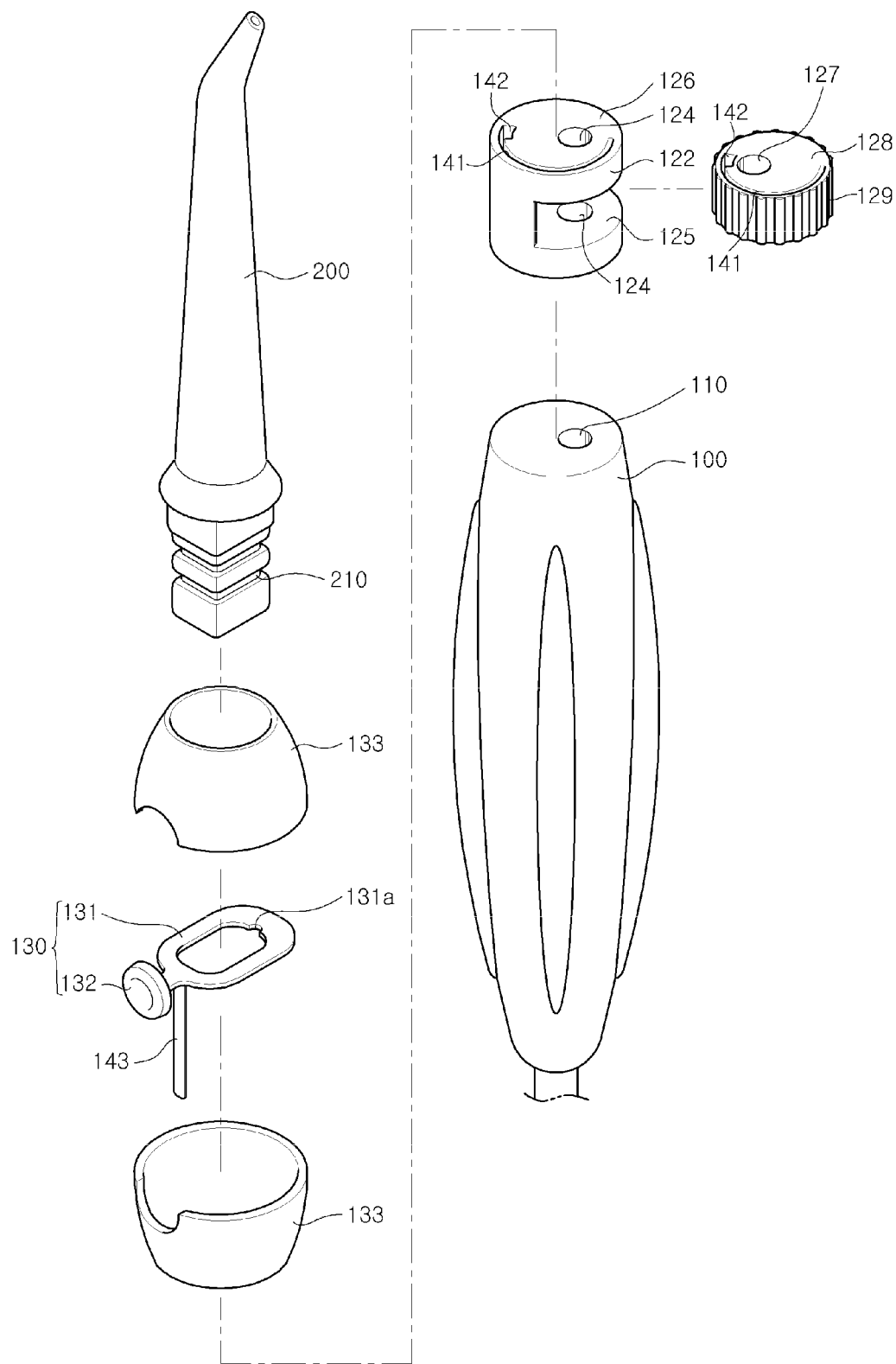
FIG. 6 is an exploded perspective view showing a structure for separating a discharge nozzle of an oral irrigator according to another embodiment of the present invention.
Figure 7:
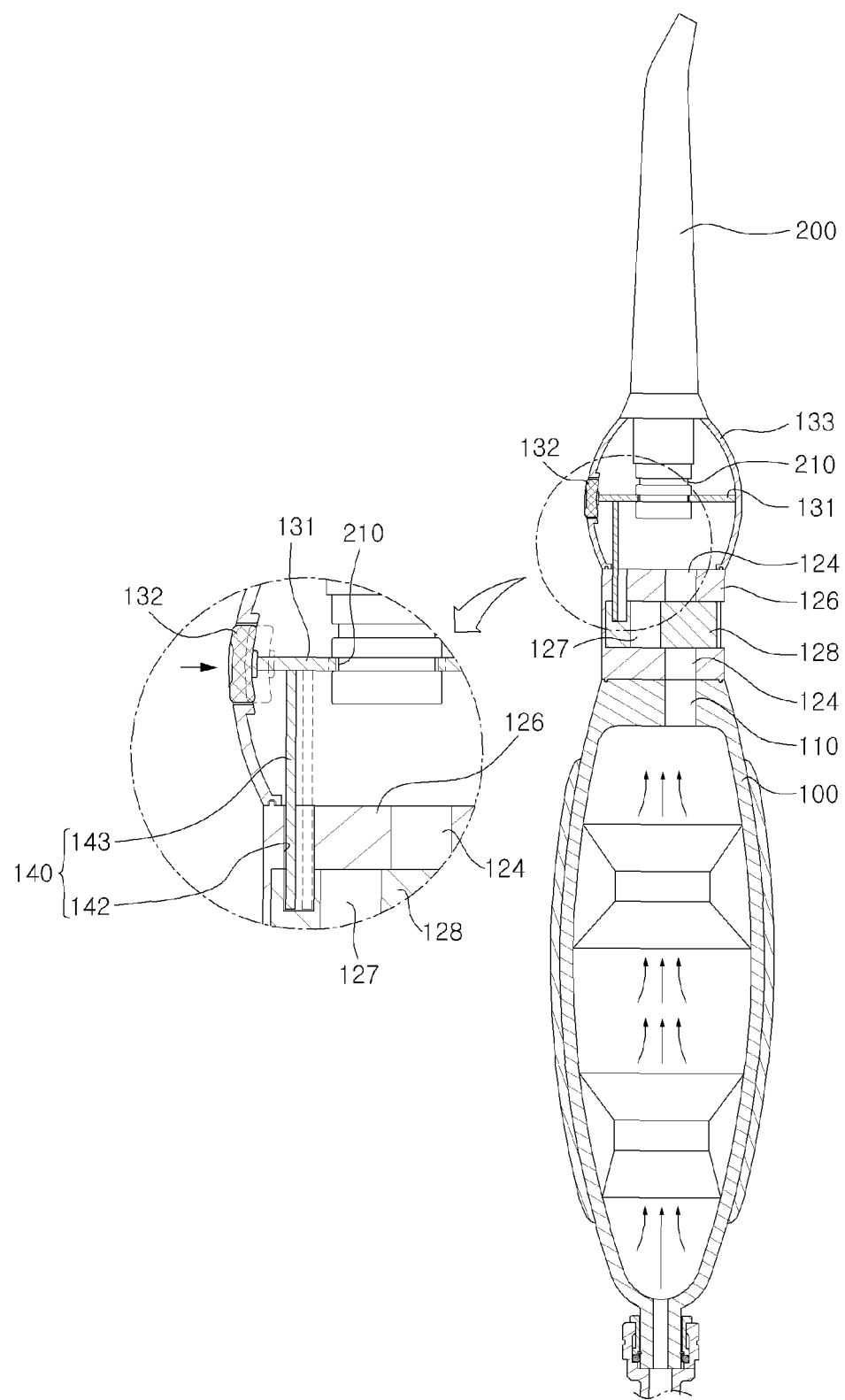
FIG. 7 is a cross-sectional view showing the structure in the state of the discharge paths being blocked.
Figure 8:
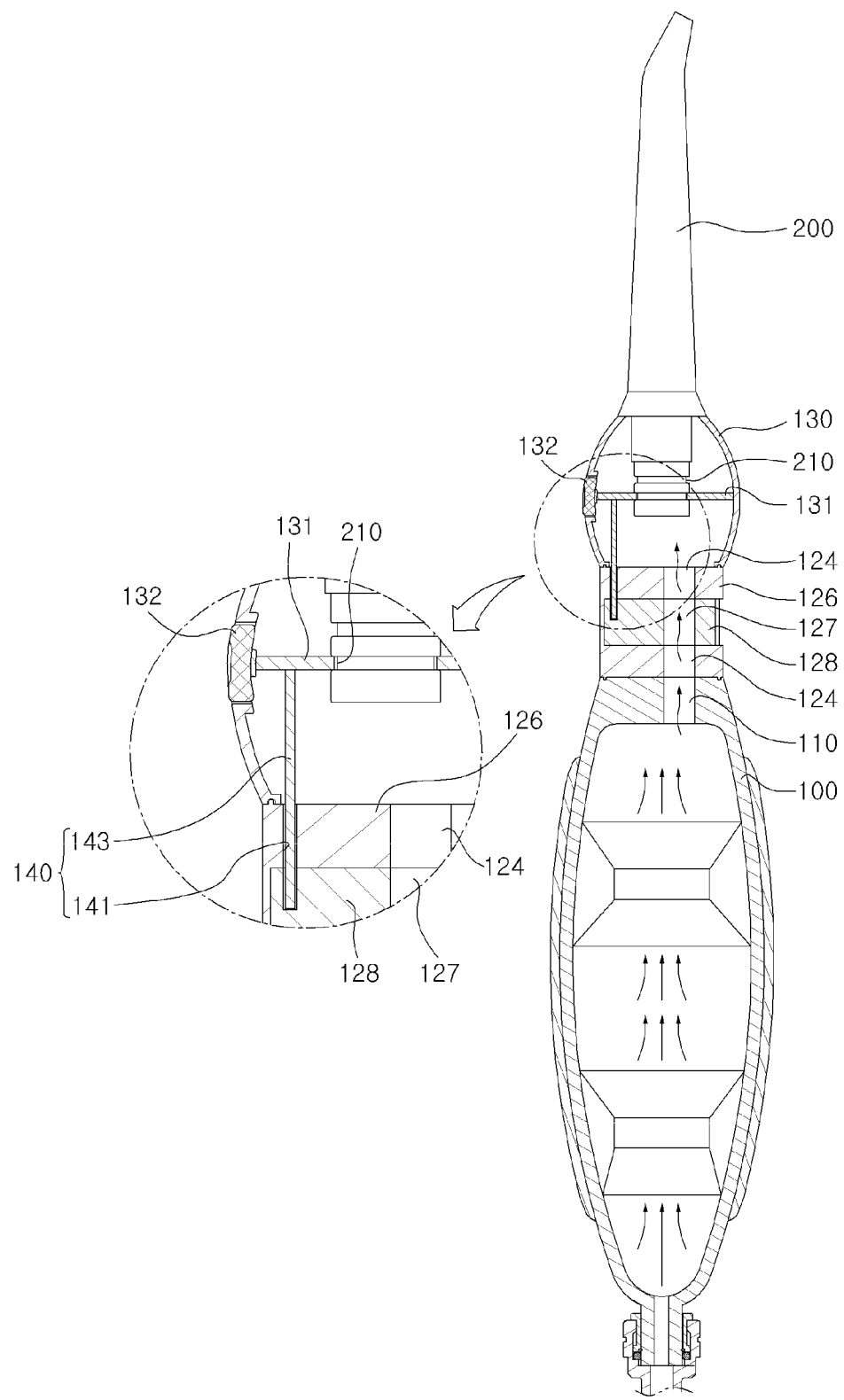
FIG. 8 is a cross-sectional view showing the structure in the state of the discharge paths being open.

FIG. 6 is an exploded perspective view showing a structure for separating a discharge nozzle of an oral irrigator according to another embodiment of the present invention, FIG. 7 is a cross-sectional view showing the structure in the state of the discharge paths being blocked, and FIG. 8 is a cross-sectional view showing the structure of the state of the discharge paths being open.

As shown in FIGS. 6 to 8, the structure for separating the discharge nozzle for an oral irrigator includes a first discharge path 110 formed in an irrigator body 100, a water pressure control lever 120, a release button section 130, and a locking section 140. Here, the constructions of the first discharge path 110 and the release button section 130 is the same as that of the first embodiment, and the construction of the water pressure control lever 120 and the locking section 140 is different from that of the first embodiment.

The water pressure control lever 120 includes an outer lever part 126 having a second discharge path 124 formed in a line with the first discharge path 110 and a central hollow receiving section 125, one side of which is open, being formed into a dual layer structure of upper and lower layers, and a central lever part 128 rotatably coupled into the receiving section 125 and having a third discharge path 127 in the other side from the central line of the irrigator body adjacent to the first and second discharge paths 110 and 120, thereby opening and blocking the first and second discharge paths 110 and 120.

Here, the outer lever part 126 is fixed to the irrigator body 100, and the central lever part 128 rotates to the left and right sides. Thus, as shown in FIG. 7, as the central lever part 128 rotates, the third discharge path 127 moves so as to gradually open the first and second discharge paths 110 and 124, or otherwise, block the first and second discharge paths 110 and 124 as shown in FIG. 8. Here, the central lever part 128 may preferably have an anti-slipping irregular outer surface 129 in order to facilitate its rotation and control.

Further, the locking section 140 includes a locking groove 141 of a certain length that extends along circumferences of the outer lever part 126 and central lever part 138, a locking release groove 142 integrally connected to one end of the locking groove 141 and having a width larger than that of the locking groove 141, and a locking bar 143 vertically protruding from an undersurface of the release button section 130 such that the locking bar is inserted into and positioned at the locking groove 141 or locking release groove 142 as the central lever part 128 rotates, so as to control the pushing operation of the release button section 130.

Here, the depth of the locking groove 141 and the locking release groove 142 is such that they pass through the upper portion of the outer lever part 126 of the dual layer structure and further extend to some extent from the upper surface of the central lever part 128.

Further, the length of the locking bar is sufficient for it to pass through the upper portion of the outer lever part 126 and enter the locking groove 141 and the locking release groove 142 that are formed in the central lever part 128.

In the above-mentioned embodiment of the structure, the operations of opening and blocking of the first and second discharge paths 110 and 124 and of pushing the release button section 130 are the same as in the first embodiment. That is, while the first and second discharge paths 110 and 124 are open and cleaning water is being sprayed, the release button section 130 for disassembling the discharge nozzle 200 cannot be operated so that the discharge nozzle 200 cannot be disassembled, and when the first and second discharge paths are blocked and the cleaning water is not sprayed, the release button section 130 can be pushed so that the discharge nozzle 200 can be disassembled.

As explained above, even if the button section is pushed by mistake while a user's mouth is being cleaned, if cleaning water is being sprayed, the release button section cannot be pushed so that the discharge nozzle cannot be disassembled, thereby preventing a safety accident from occurring. Further, if one wants to disassemble the discharge nozzle, it can be disassembled when the release button section is pushed in the state of the discharge path being blocked such that cleaning water is not sprayed, thereby improving the safety of a product.

Further, the water pressure of the spraying water can be easily regulated, and the discharge nozzle can be easily mounted and dismounted, thereby providing the effect of improving the convenience of use.

Although a preferred embodiment of the present invention has been described for the illustrated purposes, those skilled in the art will appreciate that various modifications, additions and substitutions are possible, without departing from the scope and spirit of the invention as disclosed in the accompanying claims.

What is claimed is:

1. An oral irrigator comprising:
an irrigator body;
a discharge nozzle; and
a structure-for separating a discharge nozzle of an oral irrigator from an irrigator body,
wherein the structure comprising:
a first discharge path formed in one side of the irrigator body from a central line of the irrigator body;
a water pressure control lever rotatably arranged above the first discharge path and having a second discharge path in the other side of the irrigator body from the central line, thereby opening and blocking the first discharge path;
a release button section provided on an upper portion of the water pressure control lever and into which the discharge nozzle is inserted and engaged at a central portion thereof, and configured, when an outer surface thereof is pushed, to be bent so as to release the engaged discharge nozzle; and
a locking section provided in the release button section and in the water pressure control lever to control a pushing operation of the release button section depending upon whether the first discharge path is open or blocked.

2. The structure according to claim 1, wherein the release button section includes a leaf spring part which is provided at the central portion and with which the discharge nozzle is engaged, a button part connected to one side of the leaf spring part and designed, when pushed, to bend the leaf spring part so as to enlarge an inner diameter of the leaf spring part, and a cover part covering the leaf spring part such that the button part protrudes outwardly and having an upper opening through which the discharge nozzle is inserted.

3. The structure according to claim 1, wherein the locking section includes a locking groove of a certain length that extends along a circumference of the water pressure control lever, a locking release groove integrally connected to one end of the locking groove, and a locking bar vertically protruding from an undersurface of the release button section such that the locking bar is inserted into and positioned at the locking groove or locking release groove as the water pressure control lever rotates, so as to control the pushing operation of the release button section.

4. The structure according to claim 1, wherein the water pressure control lever has an irregular outer surface in order to facilitate rotation and control of the water pressure control lever.

5. An oral irrigator comprising:
an irrigator body;
a discharge nozzle; and
a structure-for separating a discharge nozzle of an oral irrigator from an irrigator body, wherein the structure comprising:
a first discharge path formed in one side of the irrigator body from a central line of the irrigator body;
a water pressure control lever including an outer lever part having a second discharge path formed along a line with the first discharge path and a central hollow receiving section, one side of which is open, being formed into a dual layer structure of upper and lower layers, and a central lever part rotatably coupled into the receiving section and having a third discharge path in the other side of the irrigator body from the central line, thereby opening and blocking the first and second discharge paths;
a release button section provided on an upper portion of the water pressure control lever and into which the discharge nozzle is inserted and engaged at a central portion thereof, and configured, when an outer surface thereof is pushed, to be bent so as to release the engaged discharge nozzle; and
a locking section provided in the release button section and water pressure control lever to control a pushing operation of the release button section depending upon whether the first and second discharge paths are open or blocked.

6. The structure according to claim 5, wherein the locking section includes a locking groove of a certain length that extends along circumferences of the outer lever part and central lever part, a locking release groove integrally connected to one end of the locking groove and having a width bigger than that of the locking groove, and a locking bar vertically protruding from an undersurface of the release button section such that the locking bar is inserted into and positioned at the locking groove or locking release groove as the central lever part rotates, so as to control the pushing operation of the release button section.

7. The structure according to claim 5, wherein the release button section includes a leaf spring part which is provided at the central portion and with which the discharge nozzle is engaged, a button part connected to one side of the leaf spring part and designed, when pushed, to bend the leaf spring part so as to enlarge an inner diameter of the leaf spring part, and a cover part covering the leaf spring part such that the button part protrudes outwardly and having an upper opening through which the discharge nozzle is inserted.

* * * * *